(12) United States Patent
Gunn et al.

(10) Patent No.: US 6,486,127 B1
(45) Date of Patent: Nov. 26, 2002

(54) COMPOSITIONS COMPRISING D-CHIRO INOSITOL AND LIPID LOWERING COMPOUNDS AND METHODS OF TREATMENT THEREOF

(75) Inventors: Ronald Gunn, Richmond, VA (US); Geoffrey Allan, Richmond, VA (US)

(73) Assignee: Insmed, Incorporated, Glen Allen, VA (US)

( * ) Notice: Subject to any disclaimer, the term of this patent is extended or adjusted under 35 U.S.C. 154(b) by 0 days.

(21) Appl. No.: 09/984,023

(22) Filed: Oct. 26, 2001

Related U.S. Application Data
(60) Provisional application No. 60/292,529, filed on May 23, 2001.

(51) Int. Cl.$^7$ .......................... A01N 43/04; A61K 31/70
(52) U.S. Cl. ........................................... 514/25; 536/4.1
(58) Field of Search ............... 514/25, 866; 536/4.1

(56) References Cited

U.S. PATENT DOCUMENTS

| | | | | |
|---|---|---|---|---|
| 5,124,360 A | * | 6/1992 | Larner et al. ................ | 514/738 |
| 5,428,066 A | | 6/1995 | Larner et al. ................ | 514/738 |
| 5,550,166 A | | 8/1996 | Ostlund et al. .............. | 514/715 |
| 5,652,221 A | | 7/1997 | Larner et al. ................ | 514/35 |
| 5,827,896 A | * | 10/1998 | Ostlund et al. .............. | 514/715 |
| 6,020,382 A | * | 2/2000 | Doebber et al. ............. | 514/708 |
| 6,331,627 B1 | * | 12/2001 | Lohray et al. ............... | 544/284 |
| 6,337,075 B1 | * | 1/2002 | Donovan .................. | 424/236.1 |

FOREIGN PATENT DOCUMENTS

| | | |
|---|---|---|
| EP | 0 359 260 | 4/1993 |
| EP | 0 753 298 | 11/2001 |

OTHER PUBLICATIONS

Press Release, Richmond, Va, "Insmed Incorporated Announces Positive Results Of INS–1 In Patients With Type 2 Diabetes," Jan. 4, 2001.

* cited by examiner

*Primary Examiner*—James O. Wilson
*Assistant Examiner*—Patrick Lewis
(74) *Attorney, Agent, or Firm*—Stern, Kessler, Goldstein & Fox PLLC (57) ABSTRACT

The present invention relates to methods of reducing serum lipids in insulin resistant subjects comprising administration of synergistically effective amounts of D-chiro-inositol and lipid lowering medications. The present invention provides methods to treat a hyperlipidemic subject with insulin resistance comprising administration of D-chiro-inositol and a lipid lowering compound, either as concurrent single agents or as a combined composition. The methods and compositions of the present invention are particularly efficacious in treating insulin resistant subjects with a fasting blood glucose level of less than or equal to 180 mg/dL.

20 Claims, 3 Drawing Sheets

COMPOSITIONS COMPRISING D-CHIRO INOSITOL AND LIPID LOWERING COMPOUNDS AND METHODS OF TREATMENT THEREOF

CROSS-REFERENCE TO RELATED APPLICATIONS

This application claims benefit of priority to U.S. Provisional Application No. 60/292,529, filed May 23, 2001.

BACKGROUND OF THE INVENTION

1. Field of the Invention

The present invention provides methods to reduce serum lipids in insulin resistant subjects comprising administration of therapeutically effective amounts of D-chiro-inositol and lipid lowering medications. The present invention provides methods to treat a hyperlipidemic subject with insulin resistance comprising administration of D-chiro-inositol and a lipid lowering compound, either as concurrent single agents or as a combined composition. The methods and compositions of the present invention are particularly efficacious in treating insulin resistant subjects with a fasting blood glucose level of less than or equal to 180 mg/dL.

2. Related Art

Non-insulin dependent diabetes (NIDDM, or type 2 diabetes) is a worldwide health problem. According to the World Health Organization, an estimated 30 million people worldwide had diabetes in 1985. This number increased to 135 million people by 1995 and the WHO predicts a rise to 300 million people by 2025. The insidious nature of type 2 diabetes progression and medical complications that arise from hyperglycemia extract a heavy toll on the individual, healthcare resources, and society. As such, there is a continuing need for new therapeutic agents and therapeutic regimens that prevent diabetes, prevent or delay the progression of diabetes, or prevent or delay diabetic complications.

It is generally desirable to treat a subject with diabetes or at risk of developing diabetes in ways that reestablish or maintain the balance between insulin secretion and insulin sensitivity. It is highly desirable to employ methods that avoid administration of exogenous insulin. Therefore a regimen of diet and exercise is primarily used to attempt to establish more physiologic glycemic control. Sadly, however, pharmacological intervention becomes necessary. The current "second line" of therapies includes administration of pharmacological agents including sulfonylureas (e.g. GLUCOTROL®), biguanides (e.g. metformin), and PPAR gamma agonists (e.g. rosiglitazone) alone or in combination, which are used to increase endogenous insulin production, decrease hepatic glucose output, and increase periperial insulin sensitivity (Kobayashi, *Diabetes Obes. Melab.*, 1(Suppl 1): S32–S40 (1999); Brown et al., *J. Natl. Med. Assoc.*, 91(7): 389–395 (1999)). Sulfonylureas are compounds that stimulate insulin secretion from beta cells in islet tissue of the pancreas and are currently the most frequently prescribed oral hypoglycemic drugs. Increased insulin secretion by sulfonylureas may lead to hypoglycemia (Imura, *N. Engl. J. Med.*, 338: 908–909 (1998)). Unfortunately, prolonged use of sulfonylureas results in unfavorable side effects, particularly desensitization and/or apoptosis of the beta cells resulting in decreased insulin production. The effect is particularly manifest in subjects who have more severe insulin resistance in conjunction with less insulin production (Kobayashi, *Diabetes Obes. Metab.*, 1(Suppl 1): S32–S40 (1999); Kolterman et al., *Diabetes Care,* 7(Suppl 1): 81–89 (1984)). Biguanides are compounds that decrease hepatic glucose output, and thus aid in controlling hyperglycemia. PPAR gamma agonists are insulin-sensitizing compounds that increase the cell's ability to respond to smaller quantities of insulin. Eventually these therapies fail and exogenous insulin is required to maintain a balance of glucose metabolism.

Many diabetic subjects are obese and exhibit elevated levels of free fatty acids and other serum lipids. Elevated free fatty acids and other serum lipids are associated with increased insulin resistance as well as other diabetic complications including hypertension, renal failure, and cardiovascular disease inter alia.

Currently there is intensive investigation into beneficial combinations of therapies that maximize the benefit to the diabetic subject, while minimizing the side effects of the individual therapeutic agents. Despite limited in vitro and in vivo models, it is currently difficult to predict the synergistic interaction in a human of any two drugs or classes of drugs a priori.

Lipid lowering medications, principally HMG-CoA inhibitors are a well known class of drugs that are commonly used to control serum levels of lipids. Although reasonably safe, these drugs have demonstrated a significant side effect, rhabdomyolysis, a condition that results in muscle cell breakdown and release of the contents of muscle cells into the bloodstream. One drug, cerivastatin, has been withdrawn from the market. Other statins demonstrate evidence of this same side-effect, though to much less severity. Therefore it would be desirable to maintain or increase the efficacy of these drugs while administering smaller quantities of the compounds to the subjects.

There is therefore, a need for new means to control lipid levels in diabetic subjects and thus prevent the progression of diabetes and prevent or delay the onset of diabetic complications. This need and others are provided in the present invention that describes methods of treating subjects suffering from insulin resistance comprising administration of a therapeutically effective amount of D-chiro-inositol (DCI) and a therapeutically effective amount of a lipid lowering drug.

SUMMARY OF THE INVENTION

The present invention provides a method of treating a subject in need thereof comprising: (a) administration of a pharmaceutically effective amount of a D-chiro-inositol-like compound; and (b) administration of a pharmaceutically effective amount of a lipid lowering drug, wherein the effective amounts of the D-chiro-inositol and the lipid lowering drug are administered in concurrent regimens.

The combination of D-chiro-inositol and lipid lowering drugs surprisingly results in greater serum lipid control than could be achieved with either DCI alone or lipid lowering drug alone. Thus the combination of D-chiro-inositol and lipid lowering drugs allows a pharmacological treatment that enhances lipid control, prevents progression of type 2 diabetes, and ameliorates diabetic complications related to elevated lipid levels. This beneficial effect is particularly effective in insulin resistant subjects having a fasting blood glucose of less than or equal to 180 mg/dl.

The present invention provides a method of treating dyslipidemic subjects with a combination of D-chiro-inositol, or a derivative or metabolite thereof, and a lipid lowering compound. The subject may be insulin resistant and/or clinically diagnosed with a medical condition such as impaired glucose tolerance, impaired fasting glucose, diabetes, polycystic ovarian syndrome, obesity, HIV-AIDS, cachexia or other such conditions.

The present invention also provides medicinal compositions comprising (a) a pharmaceutically effective amount of a D-chiro-inositol-like compound; (b) a pharmaceutically effective amount of a lipid lowering compound; and (c) a pharmaceutically acceptable carrier.

These compositions are useful in the methods of the present invention because they provide the convenience of a single dosage unit, and therefore increase patient compliance.

DETAILED DESCRIPTION OF THE INVENTION

Definitions

The term "concurrently" as used herein refers to either administration of a single composition comprising both active agents or administration of individual compositions comprising, the two active agent administered in a time frame over which the subject receives the benefit of the combination of both active agents. As such, the subject could receive D-chiro-inositol and then the sulfonylurea or vice versa.

The phrase "a D-chiro-inositol like compound" refers to D-chiro-inositol, or a suitable derivative or metabolite thereof, or a compound containing D-chiro-inositol or a derivative or metabolite thereof. These compounds share the common functional characteristic that they can act, either directly or after in vivo metabolism as an inositol glycan substance that acts as a mediator in the cellular metabolic action of insulin (Asplin et al., *Proc. Natl. Acad. Sci.*, 90: 5924–5928 (1993)). As used herein, a "suitable derivative or metabolite" of D-chiro-inositol is a compound based on or derived from the D-chiro-inositol moiety. Illustrative examples of suitable derivatives and metabolites of D-chiro-inositol include, but are not limited to, the following: D-chiro-inositol phosphates; D-chiro-iniositol esters, preferably acctates; D-chito-inositol ethers, preferably lower alkyl ethers; D-chiro-inositol acetals; and D-chiro-inositol ketals. As used herein, a "compound containing D-chiro-inositol" is any compound that contains the D-chiro-inositol moiety as part of a larger structural composition. Illustrative examples of D-chiro-inositol containing compounds include, but are not limited to, the following: polysaccharides containing D-chiro-inositol and one or more additional sugars, such as glucose, galactose and mannose, or derivatives thereof, such as glucosamine, galactosamine and mannitol; D-chiro-inositol phospholipids; and complexes or chelates of D-chiro-inositol with one or more metal ions and the like.

The expression "prodrug" as used herein denotes a derivative of D-chiro-inositol that is converted to genuine D-chito-inositol in vivo by an enzymatic or chemical process but exhibits enhanced delivery characteristics and/or therapeutic value. The preparation and administration of prodrugs of saccharides, for example in the form of methylated or acetylated hydroxyl groups, is well known in the art. (Baker el al.,*J. Med. Chem.*, 27: 270–274 (1984)). Preferably, the methods of the present invention and the compositions of the present invention comprise an effective amount of D-chiro-inositol, pinitol (3-O—CH$_3$-D-chiro-inositol) or pinitol derivative as described in U.S. Pat. No. 5,550,166 (incorporated herein by reference), amino disaccharide insulin mimetic compounds described in U.S. Pat. No. 6,093,697 (incorporated herein by reference) or a compound containing D-chiro-inositol, including but not limited to, ciceritol (a pintol digalactoside), 1D-2-O-alpha-D-galactopyranose-chiro-inositol, fagopyritols (alpha-galactosyl-D-chito-inositol derivatives), and the like.

The term "sulfonylurea" as used herein refers to a class of compounds that have widely been used to treat diabetes by their action of stimulating production of insulin from the pancreas. Such compounds are well known, for example as described in U.S. Pat. Nos. 3,454,635, 3,669,966, 2,968,158, 3,501,495, 3,708,486, 3,668,215, 3,654,357, 3,097,242 and 4,379,785. Preferred sulfonylureas to be employed in the combinations of the present invention are glyburide (DIAβETA®, gliquidone, glipizide (GLUCOTROL®), tolbutamide, tolazamide, glisoxepid, chloropropamide (DIABINESE®), glibornuride, gliclazide, glimepiride (AMARYL®), phenbutamide, and tolcyclamide.

The term "lipid lowering medication" refers to compounds that lower cholesterol and/or triglycerides in the bloodstream, which circulate as part of lipoprotein complexes. A preferable class of lipid lowering medicines are HMG-CoA reductase inhibitors, compounds that are inhibitors of 3-hydroxy-3-methylglutaryl-CoA reductase. Compounds that have inhibitory activity for HMG-CoA reductase can be readily identified by using assays well-known in the art. For example, see the assays described or cited in U.S. Pat. No. 4,231,938 at col. 6 and WO 84/02131 at pages 30–32. Examples of HMG-CoA reductase inhibitors that may be used include, but are not limited to, lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOR®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as nivastatin and BAYCOL®; see U.S. Pat. No. 5,177,080). The term HMG-CoA reductase inhibitor as used herein includes all pharmaceutically acceptable lactone and open-acid forms (i.e. where the lactone ring is opened to form the free acid) as well as salt and ester forms of compounds which have HMG-CoA reductase inhibitory activity, and therefor the use of such salts, esters, open-acid and lactone forms is included within the scope of this invention. A second well known lipid lowering compound is gemfibrozil (LOPID®), which is typically used as an adjunctive therapeutic for lowering lipids.

List of Abbreviations

The following abbreviations are used in this application:

| | |
|---|---|
| AE | adverse event; |
| ALT (SGPT) | alanine aminotransferase (serum glutamic pyruvic transaminase); |
| ANCOVA | analysis of covariance; |
| ANOVA | analysis of variance; |
| Apo-B | apolipoprotein-B; |
| AST (SGOT) | aspartate aminotransferase (serum glutamic oxaloacetic transaminase); |
| AUC | area under the plasma-concentration time curve; |
| BMI | body mass index; |
| BUN | blood urea nitrogen; |
| C-peptide | connecting polypeptide; |
| CRF | case report form; |
| DBP | diastolic blood pressure; |
| ECG | electrocardiogram; |
| FFA | free fatty acids; |
| FPG | fasting plasma glucose; |
| GCP | good clinical practice; |
| GGT | gamma globulin transferase; |
| HbAlc | glycosylated hemoglobin; |
| HDL | high density lipoprotein; |
| ICH | International Conference on Harmonisation; |
| IND | Investigational New Drug application; |
| IRB | institutional review board; |
| ITT | intent-to-treat; |
| LDH | lactate dehydrogenase; |
| LDL | low density lipoprotein; |
| LOCF | last observation carried forward; |
| MedDRA | Medical Dictionary for Regulatory Activities; |
| MTT | meal tolerance test; |
| NEC | not elsewhere classified; |
| NOS | not otherwise specified; |
| SBP | systolic blood pressure; |
| VLDL | very low density lipoprotein; |
| WHO | World Health Organization; and |
| WHR | waist-hip ratio. |

Method of Treatment Comprising D-chiro-inositol and Lipid Lowering Medications in Diabetic Subjects The present invention provides, for the first time, beneficial therapeutic combinations of D-chiro-inositol, D-chiro-inositol metabolites, and D-chiro-inositol derivatives with lipid lowering medications in diabetic subjects. Administration of D-chiro-inositol results in improved glycemic control and reduced insulin levels in diabetic subjects as well as changes in free fatty acids and other lipids. Lipid Lowering compounds, principally statins, are used to control the level of serum lipids. Unfortunately, these lipid lowering drugs lack the desired efficacy in the diabetic population. The inventors surprisingly discovered that the combination of D-chiro-inositol and lipid lowering drugs results in serum lipid control that is superior than could be achieved with either DCI alone or the lipid lowering compounds alone.

Thus the combination of DCI and lipid lowering medications is synergistic. This provides means to either more aggressively treat hyperlipidemia or means to reduce the side effects of the lipid lowering drugs. This beneficial effect is particularly effective in insulin resistant subjects having a fasting blood glucose of less than or equal to 180 mg/dl.

Thus, the present invention comprises methods to treat a subject who suffers from insulin resistant diseases or complications that arise from hyperlipidemia comprising administration of a pharmaceutically effective amount of a D-chiro-inositol-like compound and a pharmaceutically effective amount of a lipid lowering compound, either as a single medicinal formulation or as a concurrent regimen of a D-chiro-inositol composition and a lipid lowering drug composition.

The D-chiro-inositol, metabolite or derivative thereof, or compound containing D-chiro-inositol, metabolite or derivative thereof is administered to a subject at a concentration in the range of about 3 mg/kg to about 300 mg/kg concurrently with the lipid lowering compound being administered as is known by the standard of care for the particular compound. It is well known that different lipid lowering compounds have different potency and thus require different amounts in order to achieve the desired clinical endpoint. In addition, a practitioner may alter a dosing regimen to suit the medical need of the subject, either aggressively treating the subject with a greater amount of drug or by maintaining the subject on a lesser amount of the drug.

In a preferred embodiment, the D-chiro-inositol, metabolite or derivative thereof is administered to a subject at a concentration in the range of about 25 mg/kg to about 100 mg/kg concurrently with the lipid lowering compound.

The selected dosage level will depend upon a variety of factors, including, but not limited to, the following: the route of administration; the time of administration; the rates of absorption, distribution, metabolism and/or excretion of the particular active ingredient being employed; the duration of the treatment; other drugs, compounds and/or materials used in combination with the particular active ingredients employed; the age, sex, weight, condition, general health and prior medical history of the patient being treated; and like factors well known in the medical arts. Of course, the amount of each active agent (e.g. the D-chiro-inositol and the lipid lowering compound) is also adjusted according to the level hyperlipidemia. For example more of one or both agents may be employed in a subject who is severely hyperlipidemic in order to aggressively treat the hyperlipidemic condition.

If desired, the effective daily dose of the active ingredients may be administered as one, two, three, four, five, six or more sub-doses administered separately at appropriate intervals throughout the day, optionally, in unit dosage forms.

In a preferred embodiment, the present invention provides a method of treatment comprising D-chiro-inositol and a lipid lowering compound to a subject with a fasting blood glucose level of less than or equal to 180 mg/dL.

Pharmaceutical Compositions Comprising D-chiro-inositol and a Lipid Lowering Compound The present invention provides compositions comprising:
  a pharmaceutically effective amount of a D-chiro-inositol-like compound; and
  a pharmaceutically effective amount of a lipid lowering compound;

Preferably the compositions are formulated into a dosage form typically used in the pharmaceutical arts. Thus the compositions of the present invention further may comprise a pharmaceutically acceptable carrier.

These pharmaceutical compositions will be formulated and dosed in a fashion consistent with good medical practice, taking into account the clinical condition of the individual patient (especially the side effects of treatment with the active agent), the site of delivery of the composition, the method of administration, the scheduling of administration, and other factors known to practitioners. The "pharmaceutically effective amount" of each active agent (i.e. D-chiro-inositol or a derivative thereof and the lipid lowering compound) for the purposes of the present invention is determined in view of such considerations. Those skilled in the art can readily determine empirically an appropriate "effective amount" of each active agent for a particular mammalian patient.

Preferred compositions comprise the D-chiro-inositol at a concentration of about 100 mg to about 4000 mg per unit and a lipid lowering compound in an efficacious amount. The concentration of the lipid lowering compound in the compositions of the present invention vary according with the potency of the particular active agent. Compositions comprising a D-chiro-inositol in combination with the following lipid lowering compounds are preferred by the present invention:

| Compound | Unit Dose (mg) |
| --- | --- |
| Lovastatin | 10 to 40 mg |
| Simvastatin | 5 to 80 mg |
| Pravastatin | 10 to 40 mg |
| Flustatin | 20 to 40 mg |
| Atorstatin | 10 to 40 mg |
| Cerivastatin | 0.2 to 0.4 mg. |

As used herein, the phrase "pharmaceutically acceptable" is intended to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

As used herein, "pharmaceutically acceptable carrier" is a pharmaceutically acceptable material, composition or vehicle, such as a liquid or solid filler, diluent, excipient, solvent or encapsulating material, involved in carrying or transporting the active agents of the inventive compositions from one organ, or portion of the body, to another organ, or portion of the body. Each carrier must be "acceptable" in the sense of being compatible with the other ingredients of the formulation and not injurious to the patient.

Some illustrative examples of materials which can serve as pharmaceutically-acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil. safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the inventive pharmaceutical compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, and the particular mode of administration. The amount of active ingredients that can be combined with a carrier material to produce a single dosage form will generally be that amount of each active ingredient that, together, produce the desired therapeutic effect. Generally. out of one hundred per cent, this amount will range from about 0.01 per cent to about ninety-nine percent of active ingredients, preferably from about 0.1 per cent to about 90 per cent, most preferably from about 1 per cent to about 90 per cent.

In general, the formulations are prepared by uniformly and intimately bringing into association the active ingredient with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of each active ingredient. The active ingredients of the inventive compositions may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredients can also be in micro-encapsulated form, if appropriate, with one or more of the above-described excipients.

Liquid dosage forms for oral administration of the inventive compositions include pharmaceutically acceptable emulsions, microemulsions, solutions, suspensions, syrups and elixirs. In addition to the active ingredients, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredients, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredients of the present invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active ingredients. Formulations of the present invention which are suitable for vaginal administration also include pessaries, tampons, creams, gels, pastes, foams or spray formulations containing such carriers as are known in the art to be appropriate.

Dosage forms for the topical or transdermal administration of the inventive compositions include powders, sprays, ointments, pastes, creams, lotions, gels, solutions, patches and inhalants. The active ingredient may be mixed under sterile conditions with a pharmaceutically-acceptable carrier, and with any preservatives, buffers, or propellants which may be required.

Pharmaceutical compositions of this invention suitable for parenteral administration comprise D-chiro-inositol in combination with a lipid lowering compound and one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Illustrative examples of suitable aqueous and nonaqueous carriers which may be employed in the pharmaceutical compositions of the invention include, but are not limited to, the following: water; ethanol; polyols, such as glycerol, propylene glycol, polyethylene glycol, and the like, and suitable mixtures thereof; vegetable oils. such as olive oil; and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

When the compounds of the present invention are administered as pharmaceuticals, to humans and animals, they can be given alone or as a pharmaceutical composition containing, for example, 0.01 to 99.5% (more preferably. 0.1 to 90%) of each active ingredient together in combination with at least one pharmaceutically acceptable carrier.

The preparations of the present invention may be given orally, parenterally, topically, or rectally. They are of course given by forms suitable for each administration route. Oral administration is particularly preferred.

The phrases "parenteral administration" and "administered parenterally" as used herein are intended to mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically,""peripheral administration" and "administered peripherally" as used herein are intended to mean the administration of a compound, drug or other material other than directly into the central nervous system, such that it enters the patient's system and, thus, is subject to metabolism and other like processes, for example, subcutaneous administration.

The inventive compositions may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the active ingredients of the present invention, which may be used in a suitable hydrated form, and/or the pharmaceutical compositions of the present invention, are formulated into pharmaceutically acceptable dosage forms by conventional methods known to those of skill in the art.

Therapeutic compositions can be administered with medical devices known in the art. For example, a therapeutic composition of the present invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are well known to those skilled in the art.

The following examples illustrate the present invention without, however, limiting the same thereto.

EXAMPLE 1

A randomized, placebo-controlled, double-blind clinical trial to demonstrate the efficacy of D-chiro-inositol in combination with a sulfonylurea.

Discussion of Study Design

Type 2 diabetes mellitus is a chronic disease that progresses over time. As such, a patient with diabetes cannot act as his/her own control; instead a placebo-controlled design must be used. Obese patients with type 2 diabetes mellitus were chosen as the study population because they could be reasonably anticipated to show an effect when taking D-chiro-inositol. Combining D-chiro-inositol or placebo with sulfonylureas was done in order to show the additional benefit of D-chiro-iniositol, since the targeted population had a suboptimal response to sulfonylurea treatment.

D-chiro-inositol is a moiety of an inositolphosphoglycan mediator of insulin action that is generated following insulin-stimulated hydrolysis of glycosyl phosphatidyl inositol lipids located in the cell membrane. The molecular events that couple the insulin-receptor interaction to the regulation of intracellular activity involve a complex network of signaling pathways. One particular pathway invokes an entirely novel class of low-molecular-weight inositol glycan substances as mediators of the cellular metabolic actions of insulin (Asplin el al., *Proc. Natl. Acad. Sci.*, 90: 5924–5928 (1993)). Mediators of this class are generated by a G-protein-regulated, phospholipase-catalyzed hydrolysis of inositolphosphoglycan mediators located at the outer leaflet of the cell membrane. Although different species have been identified, an inositol glycan molecule containing D-chiro-inositol and galactosamine has been characterized as playing a primary role in activating key enzymes controlling oxidative and non-oxidative metabolism of glucose.

Several lines of experimental evidence have demonstrated that a defect in the generation of D-chiro-iniositol contributes to insulin resistance. A reduction in the urinary excretion of D-chiro-inositol has been observed in Caucasian, African-American, Pima Indian, and Japanese type 2 diabetic patients. Moreover, the amount of D-chiro-inositol isolated from hemodialysate, urine, and autopsy muscle in Caucasians with type 2 diabetes mellitus is lower than the amount of D-chiro-inositol isolated from control patients (Asplin el al., *Proc. Natl. Acad. Sci.*, 90: 5924–5928 (1993)). Similar data have been obtained in rodent and primate diabetic models. The administration of D-chiro-inositol to streptozotocin-treated rats, obese Zucker rats, or normal rats that have been given a glucose load significantly improved glyceimic control (Ortineyer et al., *Endocrinology*, 132: 646–651 (1993)). In addition, D-chiro-inositol administered either by the oral or intravenous route significantly increased the disappearance rate of both plasma glucose and insulin in obese insulin-resistant rhesus monkeys (Ortmeyer el al., *Endocrinology*, 132: 646–651 (1993); Ortmeyer et al., *Nutritional Biochein.*, 6: 499–503 (1995)).

Study Objective

The objective of this study was to assess the efficacy and safety of D-chiro-inositol when administered as a single oral dose of 1200 mg/day compared to placebo, each in combination with sulfonylureas, for 3 months. Patients were required to have been on sulfonylureas for 3 months prior to study entry without reaching their target dose or with a suboptimal response.

The primary efficacy variable was change in levels of glycosylated hemoglobin (HbA1c). Secondary efficacy variables included the following:

Changes in levels of fasting insulin, fasting glucose, C-peptide, and fructosamine.

Changes in area-under-the-curve (AUC) and 120-minute insulin and glucose levels during the mcal tolerance test (MTT).

Changes in levels of triglycerides, total cholesterol, high-density lipoproteins (HDL), low-density lipoproteins (LDL), very-low-density lipoproteins (VLDL), apolipoprotein B (Apo-B), and free fatty acids (FFA).

Changes in systolic and diastolic blood pressure (SBP and DBP), body mass index (BMI), and waist-hip ratio (WHR).

Investigational Plan

Description of Overall Study Design and Plan

This multicenter, double-blind, parallel-group, placebo-controlled, randomized, fixed-dose clinical study was designed to evaluate 1200 mg/day D-chiro-inositol versus placebo in 270 obese patients with type 2 diabetes mellitus who had been receiving sulfonylureas for at least 3 months without reaching their target or with suboptimal response.

The study involved 5 scheduled visits. The first visit was the screening visit, followed by a baseline visit up to 2 weeks later. Patients were randomized at the baseline visit, half to 1200 mg/day D-chiro-inositol and half to placebo, and subsequently began 13 weeks of treatment with blinded study medication. There were 3 visits for safety and efficacy assessments, at 4, 8, and 13 weeks after beginning treatment. The 13-week visit was the final visit. Patients arrived at the investigational site in a fasted state for all visits. Assessments were to be done at the same time of day at each visit by the same responsible personnel. Medication was taken once a day at the same time of morning, except on visit days, on which the dose was delayed until just after fasting blood samples had been collected.

Dosage Schedule

Patients receiving D-chiro-inositol received four 300 mg capsules once daily for a total daily dose of 1200 mg; placebo patients took 4 placebo capsules once daily. Doses were taken orally, generally in the mornings. Patients were instructed to take their dose in the morning at the same time each day, except on visit days. On visit days, dosing was to be done at the clinic. No instructions were given regarding when to take medication in relation to meals on non-visit days.

Efficacy Assessments

Biomarkers: A meal tolerance test (MTT) was performed at baseline (Visit 2) and the final visit (Visit 5). In addition, blood was drawn at every visit for assessment of fasting glucose and insulin, HbA1c, C-peptide, fructosamine, FFA, triglycerides, total cholesterol, HDL, VLDL, LDL, and Apo-B levels.

General Procedures

All summaries and analyses were performed for each of the 2 patient groups unless otherwise indicated. All statistical tests were 2-sided and performed at the 0.05 level of significance, except for tests of treatment-by-center interaction, which were tested at the 0.10 level of significance. If the treatment-by-center interaction was statistically significant, then descriptive statistics within treatment groups were to be presented to assess the nature of the interaction. All calculations were performed using SAS Version 6.12 or higher, and Type III sums of squares were computed and used to test all hypotheses. P-values were rounded to 3 decimals. No interim analyses were conducted.

Efficacy Variables and Analyses

Primary Efficacy Variable(s) and Analyses. The primary analysis was based on the change from baseline to endpoint in HbA1c level using the modified ITT and evaluable study populations. The analysis was done using an analysis of covariance (ANCOVA) model with treatment group and the baseline HbA1c value as predictors.

Secondary Efficacy Variable (s) and Analyses. Since all secondary efficacy parameters were continuous, they were analyzed in the same manner as described above for the primary efficacy parameter, with treatment group and baseline values for the relevant parameter used as predictors. These secondary efficacy parameters included:

Fasting insulin, fasting glucose, C-peptide, and fructosamine levels;

AUC (and 120-minute) insulin and glucose levels during the MTT;

Total cholesterol, triglycerides, HDL, LDL, VLDL, Apo-B, and FFA levels;

SBP, DBP, WHR, and BMI.

Efficacy Evaluation

All patients received sulfonylureas throughout the study. The most commonly prescribed sulfonylurea medications were glyburide, taken by 38% of D-chiro-inositol-treated patients and 40% of placebo-treated patients, glipizide (44%; 39%), and glimepiride (15%; 15%). Other sulfonylurea medications reported by small numbers of patients included tolazamide, tolbutamide, and chlorpropamide.

Primary Variables

The D-chiro-inositol-treated patients in the evaluable population showed a decrease in mean HbA1c levels (%) from baseline to endpoint of 0.16, whereas placebo-treated patients showed an increase of 0.20. The difference between the groups was statistically significant (p=0.022).

TABLE 1

Primary Variable: Change in HbA1c Levels from Baseline to Week 4, Week 8, and Endpoint

| | Treatment Group | | | | |
|---|---|---|---|---|---|
| | Placebo | | D-chiro-inositol | | |
| | N | mean (SD) | N | mean (SD) | p-value* |
| For all subjects using LOCF at endpoint: | | | | | |
| Mean (in %) at baseline | 83 | 9.20 (1.11) | 82 | 8.94 (1.07) | |

TABLE 1-continued

Primary Variable: Change in HbA1c Levels from Baseline to Week 4, Week 8, and Endpoint

| | Treatment Group | | | | |
|---|---|---|---|---|---|
| | Placebo | | D-chiro-inositol | | |
| | N | mean (SD) | N | mean (SD) | p-value* |
| Mean change (in %) to endpoint | 83 | 0.20 (1.24) | 82 | −0.16 (1.03) | 0.022† |

*P-value was generated at endpoint only from an ANCOVA model with baseline value and treatment group as predictors.
†Statistically significant Subgroup Analyses Subgroup analyses were conducted in order to determine whether the efficacy of D-chiro-inositol was affected by the level of glycemic control at baseline with patients that had a FPG≦180 mg/dL and for patients that had a FPG≧180 mg/dL. As shown in Table 2 below, for evaluable patients with FPG≦180 mg/dL, D-chiro-inositol-treated patients showed a decrease in mean HbA1c level (%) from baseline to endpoint of 0.53 compared to an increase of 0.27 in placebo-treated patients; this difference of 0.80 was statistically significant (p<0.001).

TABLE 2

Subgroup Analysis: Change in HbA1c Levels from Baseline to Week 4, Week 8, and Endpoint for Patients with Fasting Plasma Glucose ≦ 180 mg/dL

| | Treatment Group | | | | |
|---|---|---|---|---|---|
| | Placebo | | D-chiro-inositol | | |
| | N | mean (SD) | N | mean (SD) | p-value* |
| For subjects with data at Week 4 | | | | | |
| Mean (in %) at baseline | 30 | 8.65 (0.94) | 35 | 8.41 (0.69) | |
| Mean change (in %) to Week 4 | 30 | −0.18 (0.57) | 35 | −0.47 (0.68) | |
| For subjects with data at Week 8 | | | | | |
| Mean (in %) at baseline | 30 | 8.65 (0.94) | 34 | 8.38 (0.67) | |
| Mean chance (in %) to Week 8 | 30 | 0.05 (1.03) | 34 | −0.57 (0.82) | |
| For all subjects using LOCF at endpoint | | | | | |
| Mean (in %) at baseline | 30 | 8.65 (0.94) | 36 | 8.42 (0.69) | |
| Mean change (in %) to endpoint | 30 | 0.27 (1.24) | 36 | −0.53 (1.03) | <0.001† |

*P-value was generated at endpoint only from an ANCOVA model with baseline value and treatment group as predictors.
†Statistically significant.

Thus the combination of sulfonylurea and D-chiro-inositol is beneficial for subjects with type 2 diabetes in general, but particularly efficacious in patients with better glycemic control (FPG≦180 mg/dL).

Secondary Variables

Observed values and changes from baseline to endpoint are summarized for the following secondary variables in the indicated tables:

Fasting insulin, fasting glucose, C-peptide, and fructosamine levels;

AUC insulin, AUC glucose, 120-minute insulin, and 120-minute glucose levels during the MTT;
Triglycerides, cholesterol, HDL, LDL, VLDL, Apo-B, and FFA levels;
Systolic and diastolic blood pressure, BMI, and WHR.

TABLE 3

Secondary Variables: Summary of Findings at Endpoint

| | Treatment Group | | | | |
| --- | --- | --- | --- | --- | --- |
| | Placebo | | D-chiro-inositol | | |
| | N | mean (SD) | N | mean (SD) | p-value* |
| AUC insulin ($\mu$U/mL·hr) | | | | | |
| Mean at baseline | 71 | 8566.4 (5127.0) | 72 | 8145.5 (3341.9) | |
| Mean change | 71 | −960.7 (3353.2) | 72 | 484.4 (2497.4) | 0.005† |
| 120-min. insulin ($\mu$U/mL) | | | | | |
| Mean at baseline | 78 | 52.67 (38.72) | 76 | 50.75 (36.10) | |
| Mean change | 78 | −6.55 (26.29) | 76 | 3.50 (25.14) | 0.011† |
| Cholesterol (mg/dL) | | | | | |
| Mean at baseline | 83 | 201.86 (31.75) | 82 | 202.10 (40.52) | |
| Mean change | 83 | 5.67 (22.96) | 82 | −2.74 (24.32) | 0.022† |
| LDL (mg/dL) | | | | | |
| Mean at baseline | 83 | 121.78 (35.18) | 82 | 121.02 (39.70) | |
| Mean change | 83 | 8.27 (24.81) | 82 | −2.95 (20.75) | 0.001† |
| Apo-B (mg/dL) | | | | | |
| Mean at baseline | 83 | 114.23 (23.06) | 82 | 115.48 (29.49) | |
| Mean change | 83 | 3.87 (13.90) | 82 | −1.26 (14.78) | 0.025† |
| FFA (mEq/L) | | | | | |
| Mean at baseline | 83 | 0.75 (0.26) | 82 | 0.69 (0.29) | |
| Mean change | 83 | −0.02 (0.31) | 82 | −0.07 (0.28) | 0.027† |

*P-value was generated at endpoint only from an ANCOVA model with baseline value and treatment group as predictors.
†Statistically significant.

Although not statistically significant in terms of good clinical practices (GCP), the inventors observed that fructosamine levels in the evaluable population mirrored HbA1c levels, with placebo-treated patients showing an increase in mean levels of 3.59 $\mu$mol/L and D-chiro-inositol-treated patients showing a decrease of 5.32 $\mu$mol/L (p=0.159).

For several lipid analyses in the evaluable population, D-chiro-inositol-treated patients had a mean decrease in analyte levels while placebo-treated patients had a mean increase, resulting in statistically significant differences. This pattern was noted for cholesterol, Apo-B, and LDL. In the analysis of FFA in the evaluable population, both treatment groups showed decreases, with D-chiro-inositol-treated patients demonstrating a statistically significantly greater decrease than placebo-treated patients.

Subgroup Analyses

Subgroup analyses to determine whether the efficacy of D-chiro-inositol was affected by the level of glycemic control diabetes at baseline were performed for all secondary variables for patients with FPG$\leq$180 mg/dL and patients with FPG>180 mg/dL. For evaluable patients with FPG>180 mg/dL, the only statistically significant finding was for LDL: placebo-treated patients had an increase of 7.47 mg/dL while D-chiro-inositol-treated patients showed a decrease of 2.02 mg/dL (p=0.036). Findings for evaluable patients with FPG$\leq$180 mg/dL are provided in Table 4 below.

TABLE 4

Secondary Variables: Summary of Findings for Evaluable Patients with Fasting Plasma Glucose $\leq$ 180 mg/dL

| | Treatment Group | | | | |
| --- | --- | --- | --- | --- | --- |
| | Placebo | | D-chiro-inositol | | |
| | N | mean (SD) | N | mean (SD) | p-value* |
| Fasting glucose (mg/dL) | | | | | |
| Mean at baseline | 30 | 154.97 (13.72) | 36 | 148.08 (21.59) | |
| Mean change | 30 | 32.07 (42.12) | 36 | 12.67 (40.16) | 0.029† |
| Fructosamine ($\mu$mol/L) | | | | | |
| Mean at baseline | 30 | 327.80 (49.14) | 36 | 321.19 (39.81) | |
| Mean change | 30 | 20.30 (60.03) | 36 | −15.22 (35.25) | 0.002† |
| AUC insulin ($\mu$U/mL·hr) | | | | | |
| Mean at baseline | 26 | 8545.8 (5174.3) | 29 | 8404.5 (3299.2) | |
| Mean change | 26 | −1267.4 (3644.9) | 29 | 1070.8 (2932.4) | 0.008† |
| 120-min. insulin ($\mu$U/mL) | | | | | |
| Mean at baseline | 30 | 57.80 (40.23) | 32 | 61.09 (47.80) | |
| Mean change | 30 | −8.92 (29.81) | 32 | 5.09 (31.75) | 0.018† |
| Cholesterol (mg/dL) | | | | | |
| Mean at baseline | 30 | 196.70 (30.66) | 36 | 192.08 (32.66) | |
| Mean change | 30 | 10.60 (19.41) | 36 | −5.31 (21.31) | 0.002† |
| LDL (mg/dL) | | | | | |
| Mean at baseline | 30 | 125.07 (31.86) | 36 | 121.36 (35.92) | |
| Mean change | 30 | 9.67 (23.40) | 36 | −4.14 (23.01) | 0.012† |
| Apo-B (mg/dL) | | | | | |
| Mean at baseline | 30 | 110.60 (24.97) | 36 | 108.89 (25.67) | |
| Mean change | 30 | 7.73 (14.57) | 36 | −4.00 (14.28) | 0.001† |

*P-value was generated at endpoint only from an ANCOVA model with baseline value and treatment group as predictors.
†Statistically significant.

Efficacy Conclusions

The primary efficacy variable was change in HbA1c levels. Patients treated with D-chiro-inositol had a decrease in mean HbA1c level (%) from baseline to endpoint of 0.16, whereas patients treated with placebo had an increase of 0.20; this difference of 0.36 was statistically significant. The effects were more pronounced in patients with FPG$\leq$180 mg/dL. Patients with FPG$\leq$180 mg/dL who were treated with D-chiro-inositol had a decrease in mean HbA1c level (%) from baseline to endpoint of 0.53, whereas patients with FPG$\leq$180 mg/dL who were treated with placebo had an increase of 0.27 (overall difference of 0.80). Fructosamine levels mirrored HbA1c levels, with placebo-treated patients having increases and D-chiro-inositol-treated patients having decreases. This difference was statistically significant for the subgroup of patients with FPG≦180 mg/dL.

Analyses of several lipid subfractions revealed statistically significant differences between D-chiro-inositol-treated and placebo-treated patients over the course of the study. For analyses of LDL, cholesterol, and Apo-B, D-chiro-inositol-treated patients had slight decreases while placebo-treated patients had relatively larger increases, resulting in statistically significant differences for the evaluable population. Results were also statistically significant for all 3 of these lipid parameters for patients with FPG≦180 mg/dL, with larger mean changes observed in this population in all instances. Both treatment groups had mean decreases in FFA levels over the course of the study. For the evaluable population as a whole, the decrease was statistically significantly greater for D-chiro-inositol-treated patients than for placebo-treated patients. These results demonstrate that patients with FPG≦180 mg/dL, who are treated with a combination of a sulonylurea and D-chiro-inositol have better glycemic control than those treated with sulfonylurea alone.

In addition, analyses of several lipids revealed statistically significant differences between D-chiro-inositol-treated and placebo-treated evaluable patients. For LDL, cholesterol, and Apo-B, D-chiro-inositol-treated patients had slight decreases in lipid levels while placebo-treated patients had relatively larger increases, resulting in statistically significant differences between groups. In the analysis of FFA levels, both groups had mean decreases. The decrease was statistically significantly greater for D-chiro-inositol-treated patients. A similar but magnified pattern was seen in patients with FPG≦180 mg/dL, with greater lipid-lowering effects observed in this population when treated with the combination of a sulfonylurea and D-chiro-inositol.

Overall, the results of this study suggest that D-chiro-inositol administered at a dose of 1200 mg/day may contribute to clinically relevant improvements in HbA1c levels and reductions in lipid levels in obese patients with type 2 diabetes mellitus.

EXAMPLE 2

D-chiro-inositol Prolongs Pancreatic Production of Insulin

Figure 1A:
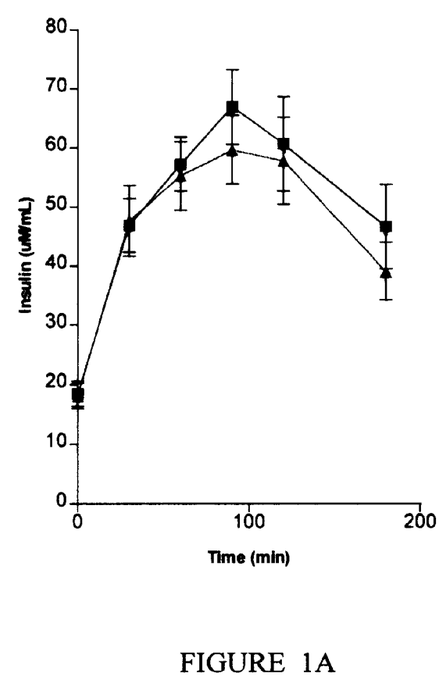
FIGS. 1A and 1B. D-chiro-inositol prolongs pancreatic production of insulin. Squares represent DCI group (DCI+SU) and triangles represent placebo (SU only). The graph on the left (1A) represents the baseline insulin AUC after a meal tolerance test for subjects with a fasting blood glucose of less than or equal to 180 mg/dl. The graph on the right (1B) represents the final (i.e. three month timepoint) insulin AUC after a meal tolerance test for subjects with a fasting blood glucose of less than or equal to 180 mg/dl. The results show that the DCI group maintains a constant insulin response over the testing period in contrast to the placebo group, which shows a decreasing capacity to secrete insulin.
Figure 1B:
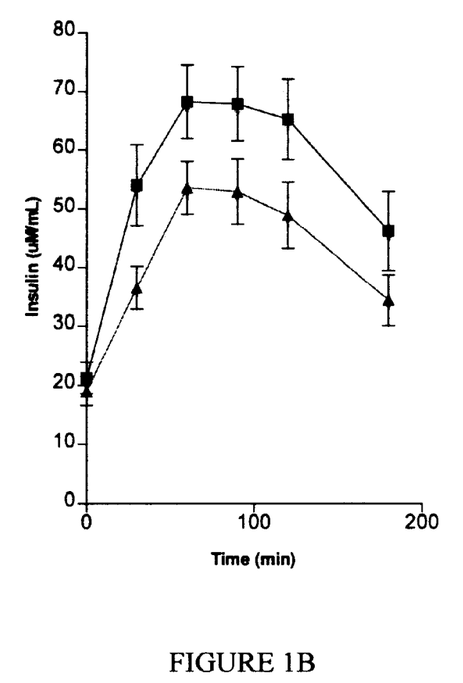
Figure 2:
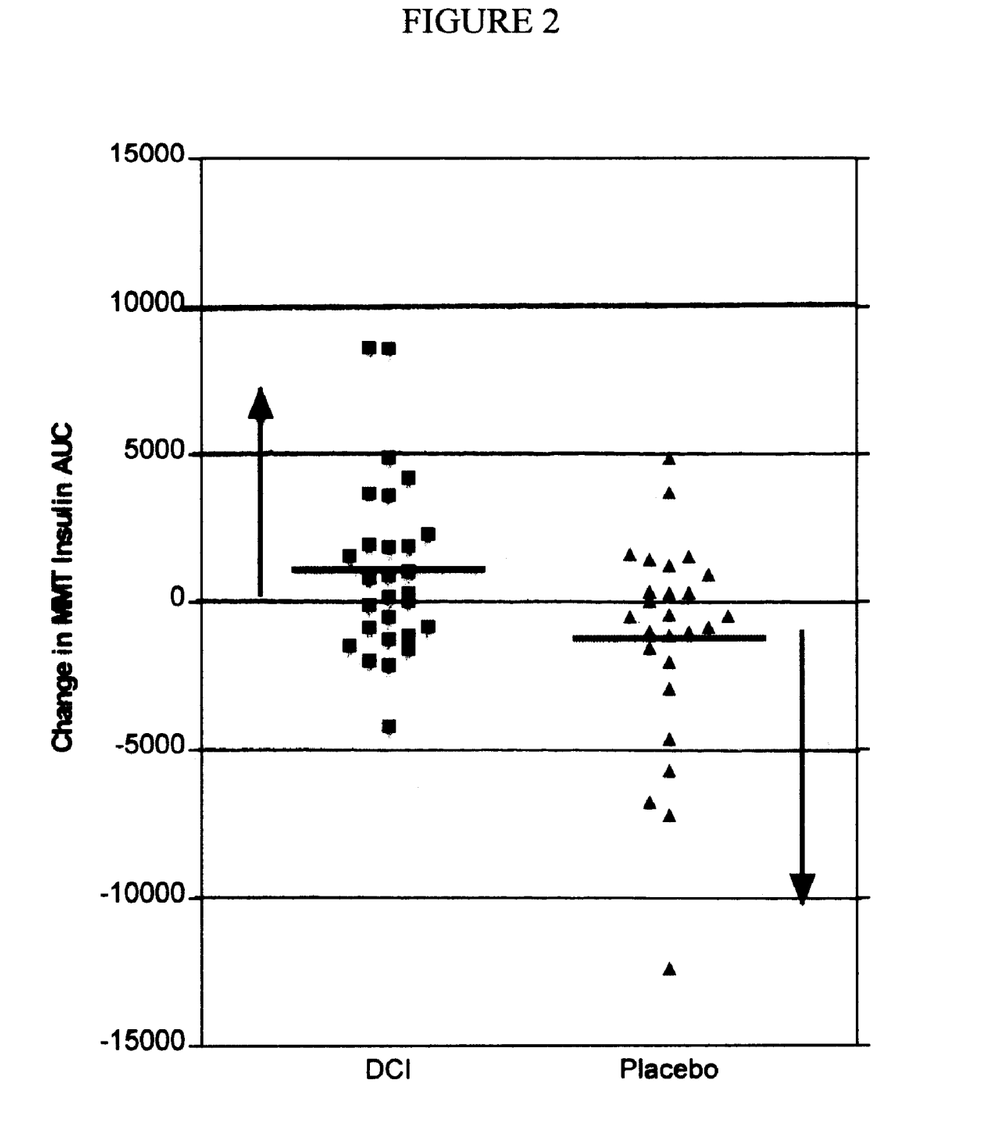
FIG. 2. Change in insulin AUC from baseline to endpoint illustrated as a scatter diagram of individual subjects. The horizontal bar indicates the median change in insulin AUC. The results show that the DCI group slightly increased the insulin AUC, while the placebo group decreased. The DCI group demonstrated no significant negative scatter (indicative of a severe reduction in insulin secretion), while the placebo group did. Conversely, the DCI group tended to scatter towards greater insulin AUC, suggesting a beneficial effect of DCI on insulin secretion or pancreatic improvement.

FIGS. 1A, 1B and 2 illustrate the observation that D-chiro-inositol (DCI) prolongs pancreatic production of insulin in patients receiving sulfonylurea compounds. FIGS. 1A and 1B show the average insulin concentration at several timepoints during a meal tolerance test challenge. At baseline, a time when the subjects had been poorly managed on SU compounds alone, both the DCI group and the SU group responded similarly in their ability to produce insulin in response to the meal challenge. Surprisingly the DCI group maintained this response after the 13 week course of treatment, while the SU group showed a declining insulin response. When the change in insulin AUC was examined for these subjects, it was noted that the DCI group demonstrated no significant negative scatter (indicative of a severe reduction in insulin secretion), while the placebo group did. Conversely, the DCI group tended to scatter towards greater insulin AUC, suggesting a beneficial effect of DCI on insulin secretion or pancreatic improvement. Instead of a homogenous decrease in insulin production by the group as a whole, the results show that a few patients significantly begin to suffer pancreatic insufficiency. It is well known that a percentage of patients receiving SU will demonstrate diabetes progression during any period of time. Without wishing to be bound by theory, the inventors contemplate that this progression is mediated by pancreatic failure and thus reduced insulin secretion. Therefore the amelioration of this effect by administration of DCI benefits the subject by the aforementioned medical improvements, but also will prevent the progression of diabetes by preventing pancreatic failure and/or decreased insulin production.

EXAMPLE 3

Subgroup Analysis of Lipid Lowering Drug /D-chiro-inositol Effects

Due to the observation of lipid lowering effects seen in the DCI group, the clinical trial described in EXAMPLE 1 was further analyzed for synergistic interactions between D-chiro-inositol and lipid lowering medications. Certain patients within the trial were treated according to standard of care with HMC-CoA inhibitors (LIPITOR®, LESCOL®, ZOCOR®, MEVACOR®, PRAVACHOL®), gemfibrozil, or a combination of HMC-CoA and gemfibrozil. No inclusion or exclusion criteria were established for the efficacy of the lipid lowering drug efficacy in the patient population. As stated supra, these patients were being sub optimally treated with a sulfonylurea prior to beginning the clinical trial. The patients could not change their lipid lowering dose and/or regimen during the length of the study.

Figure 3:
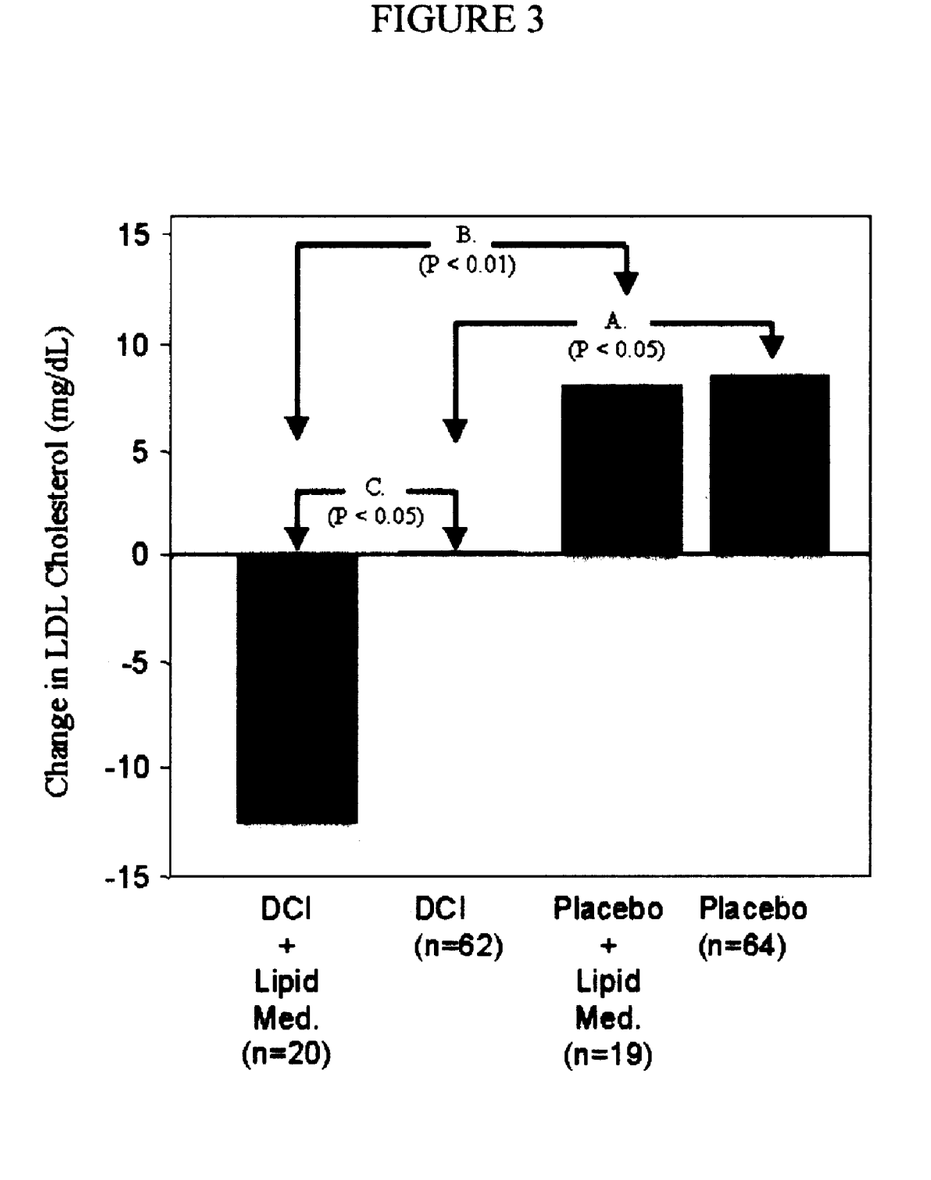
FIG. 3. D-chiro-inositol (DCI) and lipid lowering medications synergistically lower LDL cholesterol in type 2 diabetic patients. A, B, and C indicate the statistical significance comparing the two groups indicated by the downward arrows. (A) Compares the placebo group to the DCI group ($p<0.005$). (B) Compares placebo+lipid medication group to the DCI+lipid medication group ($p<0.01$). (C) Compares the DCI group to the DCI+lipid medication group ($p<0.05$).

The inventors surprisingly discovered that patients who received D-chiro-inositol and a lipid lowering medication regimen demonstrated a greater than additive reduction in LDL cholesterol than could be achieved with the lipid medications or D-chiro-inositol as single therapeutic agents. The results are shown in FIG. 3, which demonstrate that lipid lowering medications alone had little effect on preventing an increase in LDL cholesterol in diabetic patients. DCI significantly reduced the increase of LDL cholesterol. Patients who received both DCI and lipid lowering medications demonstrated a highly significant decrease in LDL cholesterol. This effect is greater than the effect of either medication alone; thus their effects are not merely additive. Without wishing to be bound by theory the inventors propose that increasing insulin responsiveness by the addition of DCI synergistically influences the benefits normally achieved by the lipid lowering medicines. This effect may be due to increased insulin responsiveness in adipocytes, where insulin is known to modulate lipolysis.

Having now fully described this invention, it will be understood to those of ordinary skill in the art that the methods of the present invention can be carried out with a wide and equivalent range of conditions, formulations, and other parameters without departing from the scope of the invention or any embodiments thereof. All patents and publications cited herein are hereby fully incorporated by reference in their entirety.

What is claimed is:

1. A method of treating dyslipidemia in a subject in need thereof comprising:
   (a) administration of synergistically effective amount of D-chiro-inositol, or a derivative or metabolite thereof, or a compound containing D-chiro-inositol or a derivative or metabolite thereof; and
   (b) administration of a synergistically effective amount of a lipid lowering compound,
   wherein said D-chiro-inositol, or derivative or metabolite thereof, or compound containing D-chiro-inositol or derivative or metabolite thereof is selected from the group consisting of: D-chiro-inositol; D-chiro-inositol-phosphates; pinitol; amino disaccharide insulin mimetics, ciceritol, 1D-2-O-alpha-D-galactopyranose, and a fagopyritol, and wherein the synergistically effective amounts of said D-chiro-inositol, or derivative or metabolite thereof, or compound containing D-chiro-inositol or derivative or metabolite thereof and the lipid lowering compound are administered as a concurrent regimen.

2. The method of claim 1, wherein the amount of D-chiro-inositol, or derivative or metabolite thereof, or compound containing D-chiro-inositol or derivative or metabolite thereof, is in the range of about 3 mg/kg to about 300 mg/kg.

3. The method of claim 1, wherein said subject has a fasting blood glucose level of less than or equal to 180 mg/dl.

4. The method of claim 1, wherein said subject is insulin resistant.

5. The method of claim 4, wherein said insulin resistant subject is clinically diagnosed with a medical indication selected from the group consisting of (A) impaired glucose tolerance; (B) impaired fasting glucose; (C) type II diabetes; (D) polycystic ovarian syndrome; (E) obesity; (F) HIV-AIDS; and (G) cachexia.

6. A method of treating dyslipidemia in a subject in need thereof comprising:
(a) administration of a synergistically effective amount of D-chiro-inositol, or a derivative or metabolite thereof, or a compound containing D-chiro-inositol or a derivative or metabolite thereof, in the range of 3 mg/kg to about 300 mg/kg, said D-chiro-inositol, or derivative or metabolite thereof, or compound containing D-chiro-inositol or derivative or metabolite thereof being selected from the group consisting of: D-chiro-inositol; D-chiro-inositol-phosphates; pinitol; amino disaccharide insulin mimetics, ciceritol, 1D-2-O-alpha-D-galactopyranose, and a fagopyritol; and
(b) administration of a synergistically effective amount of a lipid lowering compound, wherein the synergistically effective amounts of D-chiro-inositol, or derivative or metabolite thereof, or compound containing D-chiro-inositol or derivative or metabolite thereof, and the lipid lowering compound are administered concurrently.

7. The method of claim 6, wherein said D-chiro-inositol, or derivative or metabolite thereof, or compound containing D-chiro-inositol or derivative or metabolite thereof is D-chiro-inositol and is administered in the range of about 3 mg/kg to about 100 mg/kg.

8. The method of claim 7, wherein said subject is insulin resistant.

9. The method of claim 8, wherein said insulin resistant subject is clinically diagnosed with a medical indication selected from the group consisting of (A) impaired glucose tolerance; (B) impaired fasting glucose; (C) type II diabetes; (D) polycystic ovarian syndrome; (E) obesity; (F) HIV-AIDS; and (G) cachexia.

10. The method of claim 7, wherein the subject has type 2 diabetes with a fasting blood sugar level of less than or equal to 180 mg/dl.

11. A method of treating dyslipidemia in a subject in need thereof comprising:
(a) administration of D-chiro-inositol in the synergistic range of about 3 mg/kg to about 20 mg/kg; and
(b) administration of a synergistically effective lipid lowering compound;
wherein the subject suffers from type 2 diabetes with a fasting blood glucose level of less than or equal to 180 mg/dL, and wherein the synergistically effective amounts of D-chiro-inositol and the lipid lowering compound are administered concurrently.

12. A composition comprising:
(a) a pharmaceutically effective amount in the synergistic range of about 100 mg to about 4000 mg of D-chiro-inositol, or a derivative or metabolite thereof, or a compound containing D-chiro-inositol or a derivative or metabolite thereof; and
(b) a pharmaceutically effective amount of a synergistically effective lipid lowering compound,
wherein said D-chiro-inositol, or derivative or metabolite thereof, or compound containing D-chiro-inositol or derivative or metabolite thereof is selected from the group consisting of: D-chiro-inositol; D-chiro-inositol-phosphates; pinitol; amino disaccharide insulin mimetics, ciceritol, 1D-2-O-alpha-D-galactopyranose, and a fagopyritol.

13. The composition of claim 12, further comprising (c) a pharmaceutically acceptable carrier.

14. The composition of claim 12, wherein said D-chiro-inositol, or derivative or metabolite thereof, or compound containing D-chiro-inositol or derivative or metabolite thereof is D-chiro-inositol.

15. The composition of claim 12, wherein said D-chiro-inositol, or derivative or metabolite thereof, or compound containing D-chiro-inositol or derivative or metabolite thereof is D-chiro-inositol and the amount of D-chiro-inositol is selected from the group consisting of: (a) 200 mg; (b) 300 mg; (c) 400 mg; (d) 500 mg; (e) 600 mg; (f) 800 mg; (g) 1000 mg; (h) 1200 mg; and (i) 1400 mg; (j) 2000 mg; and (k) 4000 mg.

16. The composition of claim 12, wherein the lipid lowering compound is lovastatin, and wherein the amount of lovastatin is selected from the group consisting of: (a) 10 mg; (b) 20 mg; and (c) 40 mg.

17. The composition of claim 12, wherein the lipid lowering compound is simvastatin, and wherein the amount of simvastatin is selected from the group consisting of: (a) 5 mg; (b) 10 mg; (c) 20 mg; (c) 40 mg; and (c) 80 mg.

18. The composition of claim 12, wherein the lipid lowering compound is provastatin, and wherein the amount of provastatin is selected from the group consisting of (a) 10 mg and (b) 40 mg.

19. The composition of claim 12 wherein the lipid lowering compound is flustatin, and wherein the amount of flustatin is selected from the group consisting of (a) 20 mg; and (b) 40 mng.

20. The composition of claim 12 wherein the lipid lowering compound is atorvastatin, and wherein the amount of atorvastatin is selected from the group consisting of (a) 10; (b) 20 mg; and (c) 40 mg.

* * * * *